(12) United States Patent
Soeda

(10) Patent No.: US 7,084,400 B2
(45) Date of Patent: Aug. 1, 2006

(54) LATTICE STRAIN MEASURING SYSTEM AND METHOD

(75) Inventor: Takeshi Soeda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 39 days.

(21) Appl. No.: 10/845,092

(22) Filed: May 14, 2004

(65) Prior Publication Data

US 2005/0082477 A1    Apr. 21, 2005

(30) Foreign Application Priority Data

Oct. 17, 2003   (JP)   ............................. 2003-358403

(51) Int. Cl.
  *H01J 37/252*  (2006.01)
  *G1IN 23/04*  (2006.01)
  *G01N 23/20*  (2006.01)
(52) U.S. Cl. ...................... 250/311; 250/307
(58) Field of Classification Search ................ 250/311
See application file for complete search history.

(56) References Cited

U.S. PATENT DOCUMENTS 6,750,451 B1 *  6/2004  Koguchi et al. ............ 250/311

FOREIGN PATENT DOCUMENTS

| JP | 4-206941   | 7/1992 |
| JP | 7-167719   | 7/1995 |
| JP | 2000-9664  | 1/2000 |
| JP | 2001-27619 | 1/2001 |
| JP | 2001-147206| 5/2001 |

OTHER PUBLICATIONS

J.M. Zuo; Automated lattice parameter measurement from HOLZ lines and their use for the measurement of oxygen content in $YBa_2Cu_3O_{7-\delta}$ from nanometer-sized region; *Ultramicroscopy*; vol. 41; 1992; pp. 211-223./Discussed in the specification.

* cited by examiner

*Primary Examiner*—Kiet T. Nguyen
*Assistant Examiner*—James J. Leybourne
(74) *Attorney, Agent, or Firm*—Armstrong, Kratz, Quintos, Hanson & Brooks, LLP

(57) ABSTRACT

A lattice strain measuring method including the steps of: using a scanning transmission electron microscope 12 to apply convergent electron beams 34 to a sample 32 and obtain a convergent-beam electron diffraction image 36 of the sample 32; computing a lattice strain magnitude of the sample 32, based on the obtained convergent-beam electron diffraction image; and displaying the computed lattice strain magnitude, associated with an electron microscope image of the sample 32. A scanning transmission electron microscope 12 is used, whereby electron beams 34 are caused to scan to thereby suitably set an incidence position. Accordingly, the incidence position of the electron beams can be displaced at a nanometer-order pitch accurately in a short period of time. The use of a scanning transmission electron microscope 12 requires no image forming lens below the sample 32, and the convergent-beam electron diffraction image is free from the distortion due to the influence of an image forming lens. Thus, a distribution of lattice strains in an electronic device having, e.g., a micronized structure can be displayed in an image with high resolving power and with high accuracy and furthermore in a short period of time.

16 Claims, 14 Drawing Sheets

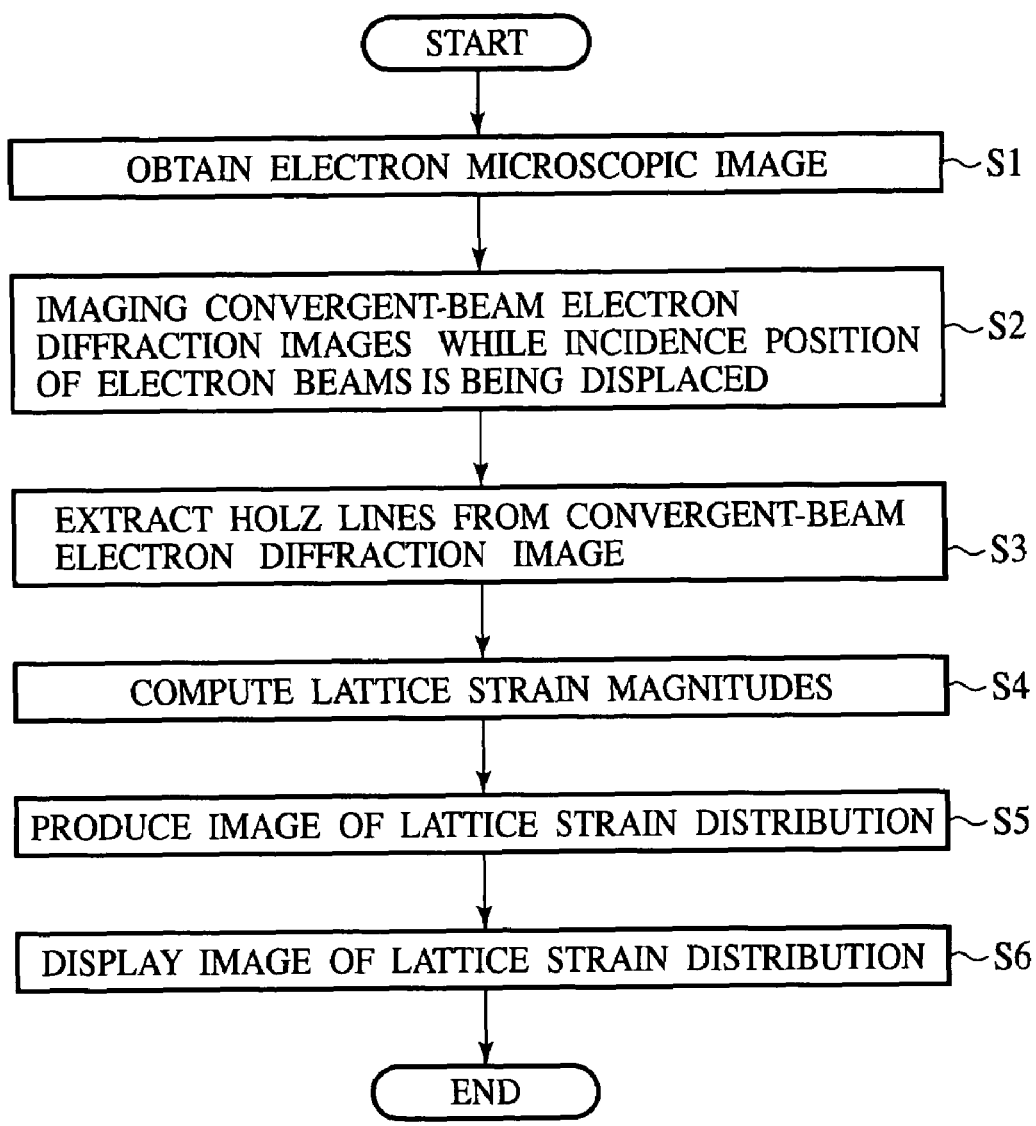

LATTICE STRAIN MAGNITUDE
$1.0 \times 10^{-2}$   $2.0 \times 10^{-2}$   $3.0 \times 10^{-2}$

LATTICE STRAIN MEASURING SYSTEM AND METHOD

CROSS-REFERENCE TO RELATED APPLICATION

This application is based upon and claims priority of Japanese Patent Application No. 2003-358403, filed on Oct. 17, 2003, the contents being incorporated herein by reference.

BACKGROUND OF THE INVENTION

The present invention relates to a lattice strain measuring system and method, and a stress measuring system and method.

Lattice strains generated in a crystalline material affect various properties of the crystalline material. Lattice strains are an important factor which much influences device characteristics especially of highly integrated and micronized ultra LSIs.

FIELD OF THE INVENTION

Conventionally, lattice strains have been measured by X-ray diffraction or Raman spectroscopy.

DESCRIPTION OF THE RELATED ART

However, these methods, whose spatial resolving power is coarse, can not be used to evaluate micronized electronic devices.

Recently, a technique of evaluating lattice strains by the convergent-beam electron diffraction method using a transmission electron microscope is proposed. In the convergent-beam electron diffraction method, converged electron beams are incident on a crystalline material to obtain a convergent-beam electron diffraction figure and change magnitudes of geometrical patterns due to lattice strains are detected to thereby give lattice strain magnitudes.

For example, Patent Reference 1 proposes a technique of evaluating lattice strains in local regions of a silicon semiconductor by convergent-beam electron diffraction method.

Patent Reference 2 and Non-Patent Reference 1 propose techniques of evaluating lattice strains of crystalline materials, such as oxide high-temperature superconductors, stainless steel, etc., other than silicon semiconductors by convergent-beam electron diffraction method.

The following references disclose the background art of the present invention.

[Patent Reference 1]
Specification of Japanese Patent Application Unexamined Publication No. 2000-9664
[Patent Reference 2]
Specification of Japanese Patent Application Unexamined Publication No. Hei 7-167719
[Patent Reference 3]
Specification of Japanese Patent Application Unexamined Publication No. 2001-147206
[Patent Reference 4]
Specification of Japanese Patent Application Unexamined Publication No. 2001-27619
[Non-Patent Reference]
J. M. Zuo, "Automated lattice parameter measurement from HOLZ lines and their use for the measurement of oxygen content in $YBa_2Cu_3O_7-\delta$ from nanometer-sized region", Ultramicroscopy, 41, (1992), p. 211–223.

SUMMARY OF THE INVENTION

An object of the present invention is to provide a lattice strain measuring system and method, and a stress measuring system and method which can understandably display lattice strain magnitudes, etc. with high resolving power and with high accuracy.

According to one aspect of the present invention, there is provided a lattice strain measuring method comprising the steps of: using a scanning transmission electron microscope to apply convergent electron beams to a sample and obtain a convergent-beam electron diffraction image of the sample; computing a lattice strain magnitude of the sample, based on the obtained convergent-beam electron diffraction image; and displaying the computed lattice strain magnitude, associated with an electron microscope image of the sample.

According to another aspect of the present invention, there is provided a lattice strain measuring method comprising the steps of: using a scanning transmission electron microscope to obtain convergent-beam electron diffraction images at respective points of a sample while an incidence position of the convergent electron beams is being moved; computing lattice strain magnitudes at the respective points of the sample, based on the obtained convergent-beam electron diffraction images; and displaying an image of a distribution of the lattice strain magnitudes of the sample, based on the computed lattice strain magnitudes.

According to further another aspect of the present invention, there is provided a stress measuring method comprising the steps of: using a scanning transmission electron microscope to apply convergent electron beams to a sample and obtain a convergent-beam electron diffraction image of the sample; computing a lattice strain magnitude of the sample, based on the obtained convergent-beam electron diffraction image; computing a stress generated in the sample, based on the computed lattice strain magnitude; and displaying a magnitude of the computed stress, associated with an electron microscope image of the sample.

According to further another aspect of the present invention, there is provided a stress measuring method comprising the steps of: using a scanning transmission electron microscope to sequentially obtain convergent-beam electron diffraction images at respective points of a sample while an incidence position of the convergent electron beams is being moved; computing lattice strain magnitudes of the respective points of the sample, based on the obtained convergent-beam electron diffraction images; computing stresses generated at the respective points of the sample, based on the computed lattice strain magnitudes; and displaying an image of a distribution of the stresses generated in the sample, based on the computed stresses.

According to further another aspect of the present invention, there is provided a lattice strain measuring system comprising: a convergent-beam electron diffraction image taking unit which uses a scanning transmission electron microscope to apply convergent electron beams to a sample and obtain a convergent-beam electron diffraction image of the sample; a lattice strain magnitude computing unit which computes a lattice strain magnitude, based on the obtained convergent-beam electron diffraction image; and a display unit which displays the computed lattice strain magnitude, associated with an electron microscope image of the sample.

According to further another aspect of the present invention, there is provided a lattice strain measuring system comprising: a convergent-beam electron diffraction image taking unit which uses a scanning transmission electron microscope to sequentially obtain convergent-beam electron diffraction images of respective points of a sample while an incidence position of convergent electron beams is being displaced; a lattice strain magnitude computing unit which computes lattice strain magnitudes at the respective points of the sample, based on the obtained convergent-beam electron diffraction images; and a display unit which displays an image of a distribution of the lattice strain magnitudes of the sample, based on the computed lattice strain magnitudes.

According to further another aspect of the present invention, there is provided a stress measuring system comprising: a convergent-beam electron diffraction image taking unit which uses a scanning transmission electron microscope to apply convergent electron beams to a sample and obtain a convergent-beam electron diffraction image of the sample; a lattice strain magnitude computing unit which computes a lattice strain magnitudes of the sample, based on the obtained convergent-beam electron diffraction image; a stress computing unit which computes a magnitude of the stress generated in the sample, based on the computed lattice strain magnitude of the sample; a display unit which displays the computed magnitude of the stress, associated with an electron microscope image of the sample.

According to further another aspect of the present invention, there is provided a stress measuring system comprising: a convergent-beam electron diffraction image taking unit which uses a scanning transmission electron microscope to sequentially form convergent-beam electron diffraction images of respective points of the sample while an incidence position of convergent electron beams is being displaced; a lattice strain magnitude computing unit which computes lattice strain magnitudes at the respective points of the sample, based on the converged-beam electron diffraction images; a stress computing unit which computes magnitudes of the stresses at the respective points of the sample, based on the computed lattice strain magnitudes; and a display unit which displays an image of a distribution of the stresses generated in the sample, based on the computed magnitudes of the stresses.

According to the present invention, a scanning transmission electron microscope is used, whereby electron beams are caused to scan to thereby suitably set an incidence position. Accordingly, the incidence position of the electron beams can be displaced at a nanometer-order pitch accurately in a short period of time. The use of a scanning transmission electron microscope requires no image forming lens below a sample, and the convergent-beam electron diffraction image is free from the distortion due to the influence of an image forming lens. Thus, according to the present invention, a distribution of lattice strains in an electronic device having, e.g., a micronized structure of nanometer order can be displayed in an image with high resolving power and with high accuracy and furthermore in a short period of time.

According to the present invention, a scanning transmission electron microscope is used, whereby data of electron microscope images associated with coordinates of respective measurement positions can be obtained. The data of electron microscope images and the data of lattice strain magnitudes are both associated with the same coordinate system, which enables an electron microscope image and the image of a lattice strain distribution can be displayed, associated with each other. According to the present invention, the image of a lattice strain distribution and an electron microscope image can be understandably displayed, associated with each other, which permits the measured results to be readily used as a useful guide for the device development.

According to the present invention, the image of a relative lattice strain magnitude distribution with respect to a lattice strain magnitude at a reference point is displayed, which makes it possible to understandably display regions where the lattice strain magnitudes are larger than the lattice strain magnitude at the reference point and regions where the lattice strain magnitudes are smaller than the lattice strain magnitude at the reference point. When a point having no lattice strain is the reference point, regions having compression strains and regions having tensile strains can be understandably displayed.

According to the present invention, stresses in respective points of a sample are computed, based on lattice strain magnitudes given by the lattice strain measuring system and method described above, whereby distributions of stresses generated in an electronic device of a micronized structure can be displayed in images with high resolving power and high accuracy and furthermore in a short period time. Furthermore, a stress distribution image can be understandably displayed, associated with an electron microscope image, which makes it possible to use the measured results to be used as a useful guide in the device development.

According to the present invention, distributions of relative stress magnitudes with respect to a magnitude of a stress generated in a reference point R are displayed in images, which makes it possible to understandably display regions where stresses of larger magnitudes than the magnitude of the stress generated in the reference point and regions where stresses of smaller magnitudes than the stress magnitude in the reference point.

BRIEF DESCRIPTION OF THE DRAWINGS

FIG. 3 is the flow chart of the lattice strain measuring method according to the first embodiment of the present invention.

DETAILED DESCRIPTION OF THE EXEMPLARY EMBODIMENTS

The above-mentioned proposed measuring method, in which an operator operates to displace an incidence position of electron beams, takes a longtime for the alignment. Accordingly, it is very difficult in terms of time and cost to measure strain magnitudes at a number of points. Since the incidence position of electron beams are displaced by the operator's operation, it is impossible to set the incidence position of electron beams with high accuracy. In the other proposed measuring methods, a sample is displaced to change an incidence position of electron beams, but it is very difficult to displace the sample accurately by a very fine distance in a short period of time. For example, it is very difficult to displace a sample by a nanometer-order pitch accurately and in a short period of time. Thus, these proposed methods cannot measure lattice strain magnitudes of electronic devices of nanometer-order structures. Furthermore, in these proposed methods, which use TEMs (Transmission Electron Microscopes), the convergent-beam electron diffraction images are distorted by the influences of image forming lenses disposed below samples, which makes it impossible to give strain magnitudes with high accuracy. Furthermore, the proposed measuring methods cannot precisely align measuring points with an electron microscope image and cannot be a useful guide for the device development.

A First Embodiment

Figure 1:
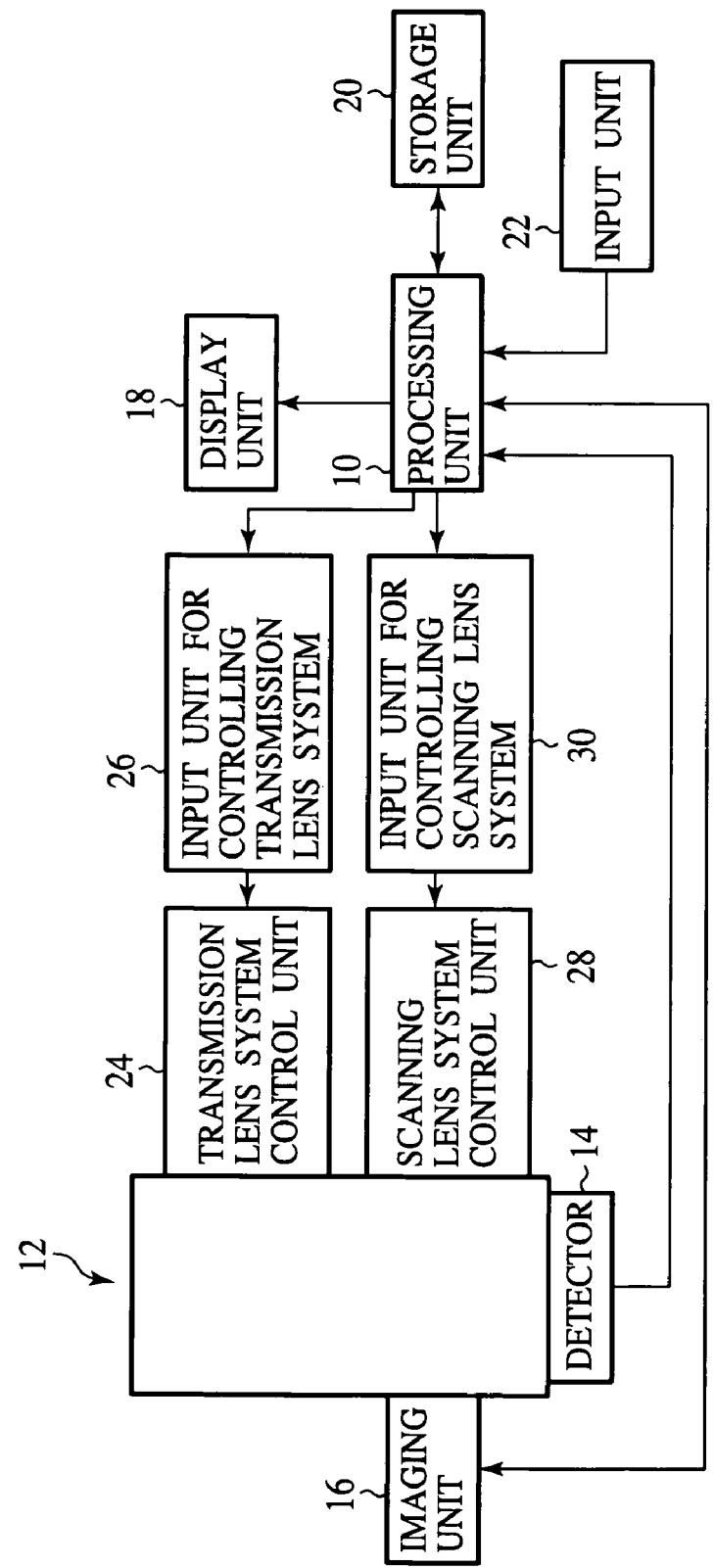
FIG. 1 is a block diagram of the lattice strain measuring system according to a first embodiment of the present invention.
Figure 2:
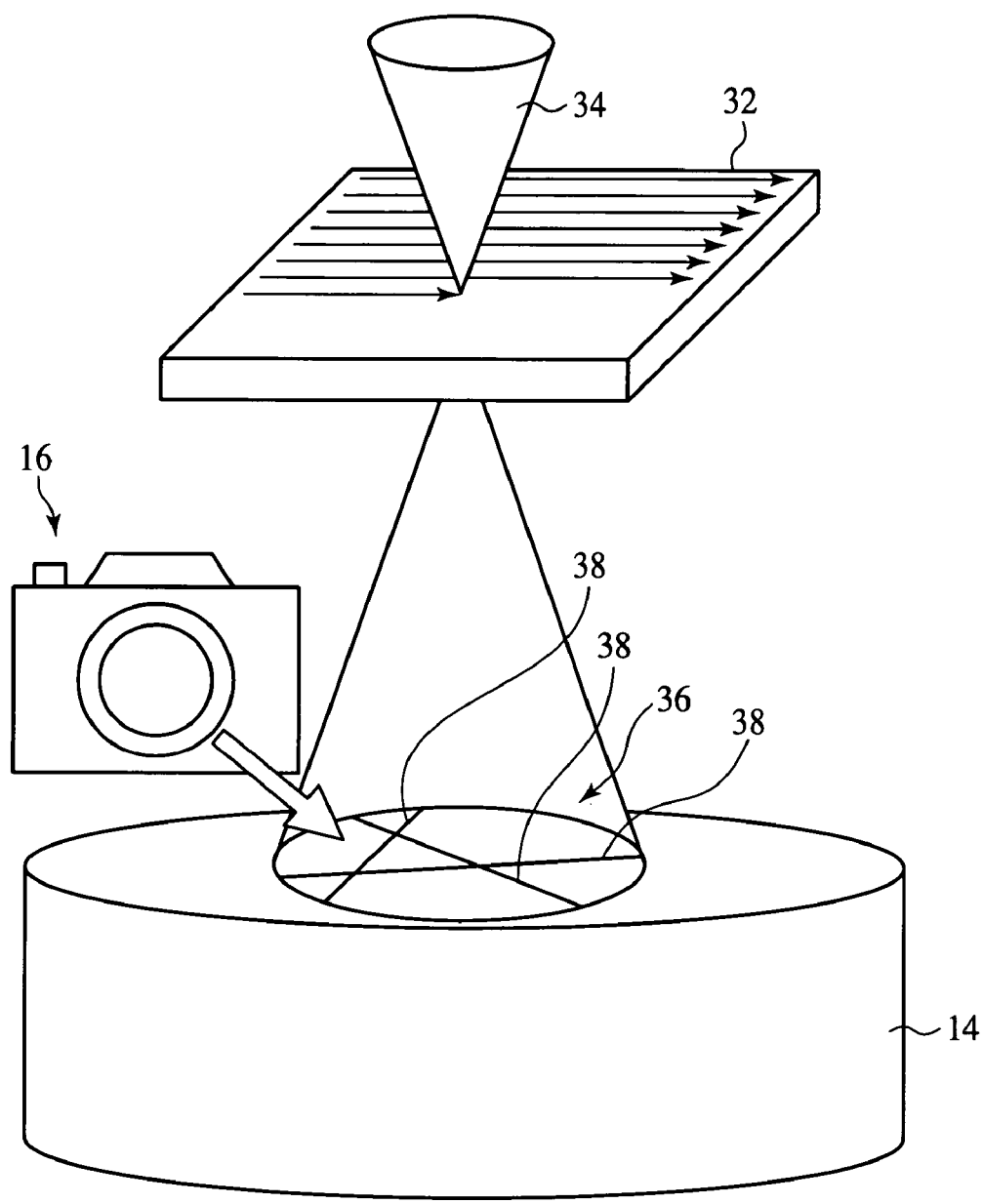
FIG. 2 is a view of a part of the lattice strain measuring system according to the first embodiment of the present invention.

The lattice strain measuring system and method according to a first embodiment of the present invention will be explained with reference to FIGS. 1 to 6. FIG. 1 is a block diagram of the lattice strain measuring system according to the present embodiment. FIG. 2 is a view of a part of the lattice strain measuring system according to the present embodiment.

(The Lattice Strain Measuring System)

The lattice strain measuring system according to the present embodiment will be explained with reference to FIGS. 1 and 2.

As shown in FIG. 1, the lattice strain measuring system according to the present embodiment comprises a processing unit 10 which generally controls the measuring system and performs prescribed processing, an STEM (Scanning Electron Transmission Microscope) 12, a detector 14 which is disposed below the part where a sample is to be mounted and detects magnitudes of electron beams transmitted by the sample, imaging unit 16 which takes pictures of convergent-beam electron diffraction images 36 (see FIG. 2) appearing on the surface of the detector 14, and a display unit 18 which displays measured results, etc.

The imaging unit 16 can be, e.g., a camera with a CCD mounted on. The imaging unit 16 is not essentially as shown in FIG. 1. The imaging unit 16 is not essentially a camera with a CCD mounted on and can be any other suitable imaging unit.

The processing unit 10 can be, e.g., a personal computer. The processing unit 10 is not essentially a personal computer and can be an industrial use computer or others.

The storage unit 20 is connected to a processing unit 10. The storage unit 20 temporarily or continuously stores various data, as of measured results, etc. The storage unit 20 can be, e.g., a hard disc, a RAM or others. Programs for performing prescribed processing and control by processing unit 10 are installed in the storage unit 20.

The processing unit 10 is connected to an input unit 22 for inputting commands by operators. The input unit 22 can include, e.g., a key board, a mouse, etc.

The scanning transmission electron microscope 12 includes a transmission lens system control unit 24 for controlling the transmission lens system of the scanning transmission electron microscope 12. An input unit for controlling the transmission lens system 26 is inserted between the processing unit 10 and the transmission lens system control unit 24. The input unit for controlling the transmission lens system 26 controls the transmission lens system control unit 24, based on signals outputted by the processing unit 10. The processing unit 10 can control the transmission lens system of the scanning transmission electron microscope 12 by using the input unit for control the transmission lens system 26 and the transmission lens system control unit 24.

The scanning transmission electron microscope 12 includes a scanning lens system control unit 28 which controls the scanning lens system of the scanning transmission electron microscope 12. An input unit for controlling the scanning lens system 30 is inserted between the processing unit 10 and the scanning lens system control unit 28. The input unit for controlling the scanning lens system 30 controls the scanning lens system control unit 28, based on signals outputted by the processing unit 10. The processing unit 10 uses the input unit for controlling the scanning lens 30 and the scanning lens system control unit 28 to control the scanning lens system of the scanning transmission electron microscope 12. For example, the processing unit 10 can cause electron beams to scan a sample and can stop the incidence position of the electron beams at a desired point.

The scanning transmission electron microscope (STEM) 12 is an electron microscope different from the transmission electron microscope (TEM), in which, as shown in FIG. 2, convergent electron beams 34 are caused to scan a sample 32, electron diffraction intensities and electron scattering intensities at respective incidence positions of the electron beams 34 are detected by the detector 14 to thereby display electron microscope images. The scanning transmission electron microscope 12 requires no image forming lens, etc. to form electron microscope images, and accordingly, the electrons transmitted by a sample 32 are free from the influence of the aberration of image forming lenses. Accordingly, the convergent-beam electron diffraction images given by the scanning transmission electron microscope 12 are free from the influence of strains due to the lens.

The convergent-beam electron diffraction image is a diffraction image given by applying convergent electron beams to a sample. In the convergent-beam electron diffraction image 36, a plurality of high order diffraction lines, i.e., HOLZ (High Order Laue Zone) lines 38 which are formed by convergent electron beams being reflected on the lattice planes of the crystals when the convergent electron beams pass through the interior of a sample.

The scanning transmission electron microscope 12, which requires no image forming lens, etc., is invulnerable to color aberration in comparison with the transmission electron microscope and can observe relatively thick samples 32. To obtain clear convergent-beam electron diffraction images, it is advantageous that relatively thick samples 32 can be observed. This is because HOLZ lines 38, which are geometric patterns appearing in the convergent-beam electron diffraction images, are clearer as the sample 32 is thicker. The HOLZ lines 38 are clearer as the sample 32 is thicker because the HOLZ lines 38 are generated by inelastic scattering. The inelastic scattering means that electrons incident on the sample 32 lose energy and scatters when the electrons scatter. The inelastic scattering more tends to take place as the sample 32 is thicker. Accordingly, the HOLZ lines 38 are clearer as the sample 32 is thicker, and fine changes of the HOLZ lines due to lattice strains can be detected.

Signals of the intensities of the electron beams detected by the detector 14 are inputted to the processing unit 10. The processing unit 10 associates the data of the intensities of the electron beams detected by the detector 14 with coordinates of the respective measuring points. The data of the intensities of the electron beams associated with the coordinates of the respective measuring points are stored in the storage unit 20.

When a convergent-beam electron diffraction image 36 is given, the processing unit 10 controls the scanning lens system to stop the incidence position of electron beams 34 sequentially at respective measuring points. When the processing unit 10 stops the incidence position of the electron beams 34, the processing unit 10 outputs to the imaging unit 16 a signal commanding the imaging unit 16 to take a convergent-beam electron diffraction image 36 at the measuring point.

The imaging unit 16 sequentially takes convergent-beam electron diffraction images 36 appearing on the surface of the detector 14. The imaging unit 16 can be, e.g., a slow scan CCD camera.

The image data of the convergent-beam electron diffraction images 36 are inputted to the processing unit 10. The data of the convergent-beam electron diffraction images 36 inputted to the processing unit 10 are associated with coordinates of the respective measuring points and are sequentially stored in the storage unit 20.

The processing unit 10 computes lattice strain magnitudes of the respective measuring points, based on the convergent-beam electron diffraction images 36 at the respective measuring points. The method of computing the lattice strain magnitude will be detailed later. The lattice strain magnitudes of the respective measuring points computed by the processing unit 10 are stored in the storage unit 20 as data associated with the coordinates of the respective measuring points. The processing unit 10 produces an image of a distribution of the lattice strains, based on the computed lattice strain magnitudes of the respective measuring points.

The processing unit 10 displays the lattice strain distribution image on the screen of the display unit 18. When the lattice strain distribution image is displayed, the image is displayed, associated with the electron microscope image of the sample 32. The lattice strain distribution image can be displayed, associated with the electron microscope image of the sample because the data of lattice strain magnitudes at respective measuring points and the data of the electron microscope image are associated with the same coordinate system. The display unit 18 can be, e.g., a CRT, liquid crystal display or others. The electron microscope image of the sample can be printed out by a printer (not shown).

The lattice strain measuring system according to the present embodiment is thus constituted.

(The Lattice Strain Measuring Method)

Next, the lattice strain measuring method according to the present embodiment will be explained with reference to FIG. 3. FIG. 3 is a flow chart of the lattice strain measuring method according to the present embodiment.

While the transmission lens system and the scanning lens system are controlled to cause electron beams 34 to scan, intensities of the electron beams transmitted by a sample 32 are detected by the detector 14. Signals of the intensities of the electron beams detected by the detector 14 are inputted to the processing unit 10. The processing unit 10 associate the data of the intensities of the electron beams detected by the detector 14 with coordinates of respective measuring points. The data of the intensities of the electron beams associated with the coordinates of the respective measuring points are stored in the storage unit 20.

Then, the processing unit 10 produces an electron microscope image, based on the data of the intensities of the electron beams associated with the coordinates of the respective measuring points. The data of the produced electron microscope image are stored in the storage unit 20.

Thus, the electron microscope image of the sample is obtained (Step S1).

Then, the processing unit 10 displays the produced electron microscope image by the display unit 18.

Then, an operator indicates regions for the lattice strain to be measured in by the input unit 22 while watching the electron microscope image displayed on the screen of the display unit 18.

Then, the processing unit 10 controls the scanning lens system to stop the scan of the electron beams 34 at a point where the lattice strain magnitude is to be measured. When electron beams 34 are incident on the sample 32, the electron beams 34 are incident on the sample 32 in, e.g., [230] direction. The electron beams 34 are applied in [230] direction, because when the electron beams 34 are applied in [230] direction, a number of HOLZ lines 38 appear in the converge electron diffraction image 36.

Electron beams 34 are incident on the sample 32 in [230] direction in the present embodiment but are not essentially incident in [230] direction. A direction in which electron beams 34 are to be applied is suitably set so as to obtain a desired convergent-beam electron diffraction image 36.

Then, the convergent-beam electron diffraction image 36 appeared on the surface of the detector 14 is taken by the imaging unit 16.

Figure 4A:
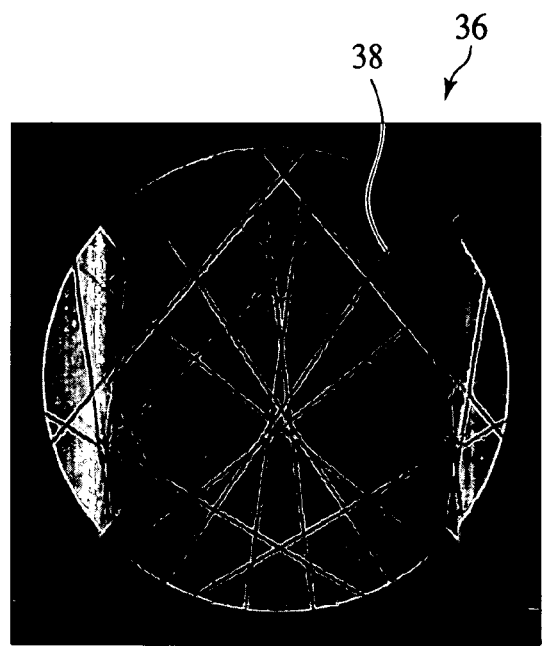
FIGS. 4A and 4B are views of a convergent-beam electron diffraction image.

FIG. 4A is a view of a convergent-beam electron diffraction image taken by a slow scan CCD camera. As seen in FIG. 4A, a number of HOLZ lines 38 appear in the convergent-beam electron diffraction image 36. The image data of the convergent-beam electron diffraction image 36 taken by the imaging unit 16 is inputted in the processing unit 10.

Then, the processing unit 10 stores the image data of the convergent-beam electron diffraction image 36 associated with coordinates of the measuring points in the storage unit 20.

Then, the processing unit 10 controls the scanning lens system to thereby displace the incidence position of the electron beams 34 on the sample 32. For example, when a lattice strain distribution is measured with a 1 nm resolving power, the incidence position of the electron beams 34 is displaced by 1 nm. Thus, the incidence position of the electron beams 34 is displaced to a next measuring point.

A lattice strain distribution is measured with a 1 nm resolving power in the present embodiment, but the resolving power is not essentially limited to 1 nm. A pitch at which the incidence position of the electron beams 34 is displaced is suitably set so that a lattice strain distribution can be displayed with a desired resolving power.

Then, as described above, the convergent-beam electron diffraction image 36 appearing on the surface of the detector 14 is taken by the imaging unit 16. The data of the convergent-beam electron diffraction image 36 taken by the imaging unit 16 is inputted to the processing unit 10, as described above.

Then, as described above, the processing unit 10 associates the data of the convergent-beam electron diffraction image 36 with coordinates of the measuring points and stores in the processing unit 10, as described above.

Then, as described above, the scanning lens system is controlled to move the incidence position of the electron beams 34 sequentially to points where the lattice strain is to be measured. The imaging unit 16 sequentially takes convergent-beam electron diffraction images 36 appearing on the surface of the detector 14 at the respective measuring points. The data of the convergent-beam electron diffraction images 36 are sequentially inputted in the processing unit 10, as described above. As described above, the processing unit 10 associates the data of the convergent-beam electron diffraction images 36 at the respective measuring points with coordinates of the respective measuring points and stores in the storing unit 20. The timing of setting the incidence position of the electron beams 34 at a measuring point and the timing of shuttering the imaging unit 16 are suitably synchronized, whereby the convergent-beam electron diffraction images 36 at the respective measuring points of the sample 32 can be smoothly took.

Thus, data of the convergent-beam electron diffraction images 36 at the respective measuring points in a region for the lattice strain to be measured are obtained (step S2).

Then, based on the thus obtained data of the convergent-beam electron diffraction images 36, lattice strain magnitudes of the respective measuring points are computed. The method for computing the lattice strain can be the lattice strain measuring method described in the specification of Japanese Patent Application No. 2002-236663 filed by the applicant of the present application.

The method for computing the lattice strain magnitude is not essentially the measuring method described in the specification of Japanese Patent Application No. 2002-236663 and can be another method. However, in order to measure the lattice strain magnitude with high accuracy, the measuring method described in the specification of Japanese Patent Application No. 2002-236663 is advantageous.

The lattice strain magnitude measurement will be explained in the present embodiment by means of the measuring method described in the specification of Japanese Patent Application No. 2002-236663.

First, HOLZ lines 38 are extracted from a convergent-beam electron diffraction image 36. In extracting the HOLZ lines 38, Hough transform, for example, is used. In Hough transform, a straight line is extracted by using a length and an angle of a vertical line drawn from an origin to a straight line. In the Hough transform, first, respective coordinates (i, j) of an original image are transformed into curves expressed by trigonometric functions. Each of coordinates $(\rho, \theta)$ of the transformed image is expressed by a distance $\rho$ between the coordinates and the origin of the original image and an angle $\theta$. Then, intersections $(\rho_0, \theta_0)$ of a plurality of transformed curves are given, and the given intersections $(\rho_0, \theta_0)$ are inversely transformed. Because the coordinates $(\rho_0, \theta_0)$ of the intersections, a distance $\rho_0$ and an angle $\theta_0$, have been uniquely decided, an image given by the inverse transform is a straight line. The HOLZ lines 38 are thus extracted from the convergent-beam electron diffraction image 36 (step S3).

Figure 4B:
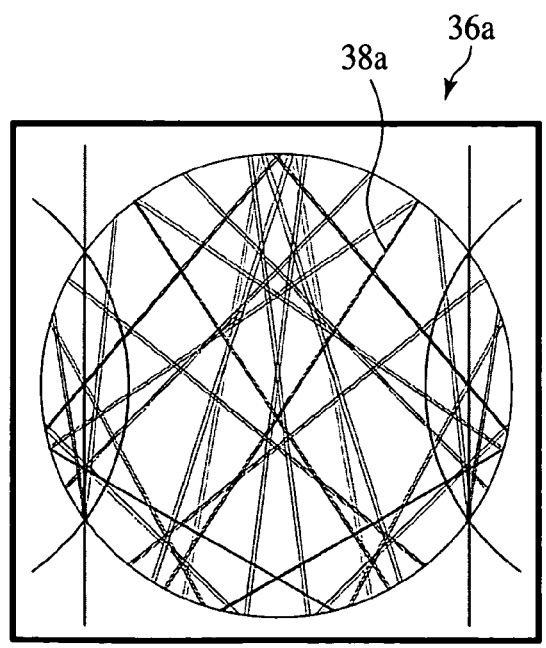

Then, the convergent-beam electron diffraction image 36 given by the Hough transform and a convergent-beam electron diffraction image 36a given by theoretical computation are compared with each other to give lattice strain magnitudes. FIG. 4B is a view of a convergent-beam electron diffraction image given by the theoretical computation. In giving lattice strain magnitudes, the convergent-beam electron diffraction image 36 extracted by the Hough transformed and the convergent-beam electron diffraction image 36a given by the theoretical computation are compared with each other to give a parameter which minimizes a difference between both of them so as to give an optimum solution. In giving lattice strain magnitudes, simplex method, for example, is used. Simplex method is useful to give a minimum value of a function having a plurality of parameters. For the decision, $\chi^2$ is used. When a distance between the intersections of the HOLZ lines 38 of the convergent-beam electron diffraction image 36 extracted by the Hough transform is represented by $D_e(n)$, and a distance between the intersection between the HOLZ lines 38a of the convergent-beam electron diffraction image 36a given by the theoretical computation is represented by $D_c(n)$, the following formula is given:

$$\chi^2 = \frac{\sum_{n=1}^{m}(D_e(n) - D_c(n))^2}{\sum_{n=1}^{m} De(n)^2} \quad (1)$$

wherein "m" represents a numbers of distances between intersections to be measured.

The inter-intersection distance $D_c(n)$ of the HOLZ lines 38a of the convergent-beam electron diffraction image 36a given by the theoretical computation changes by changing a lattice strain magnitude, which is a parameter. While lattice strain magnitudes of the theoretical computation are being suitably set, $\chi^2$ values are respectively computed, and a theoretical lattice strain magnitude which minimizes the value of $\chi^2$ is given. A theoretical lattice strain magnitude which minimizes the value of $\chi^2$ is an optimum solution. Thus, the lattice strain magnitude can be computed with high accuracy.

Then, as described above, lattice strain magnitudes at the respective measuring points are sequentially computed. Thus, lattice strain magnitudes at the respective measuring points of the sample are measured (step S4).

For the details of the measuring method, refer to the specification of Japanese Patent Application No. 2002-236663.

Then, the processing unit 10 produces an image of the lattice strain distribution, based on the computed lattice strain magnitudes at the respective measuring points (step S5). The data of the lattice strain distribution image is stored in the storage unit 20.

Figure 5:
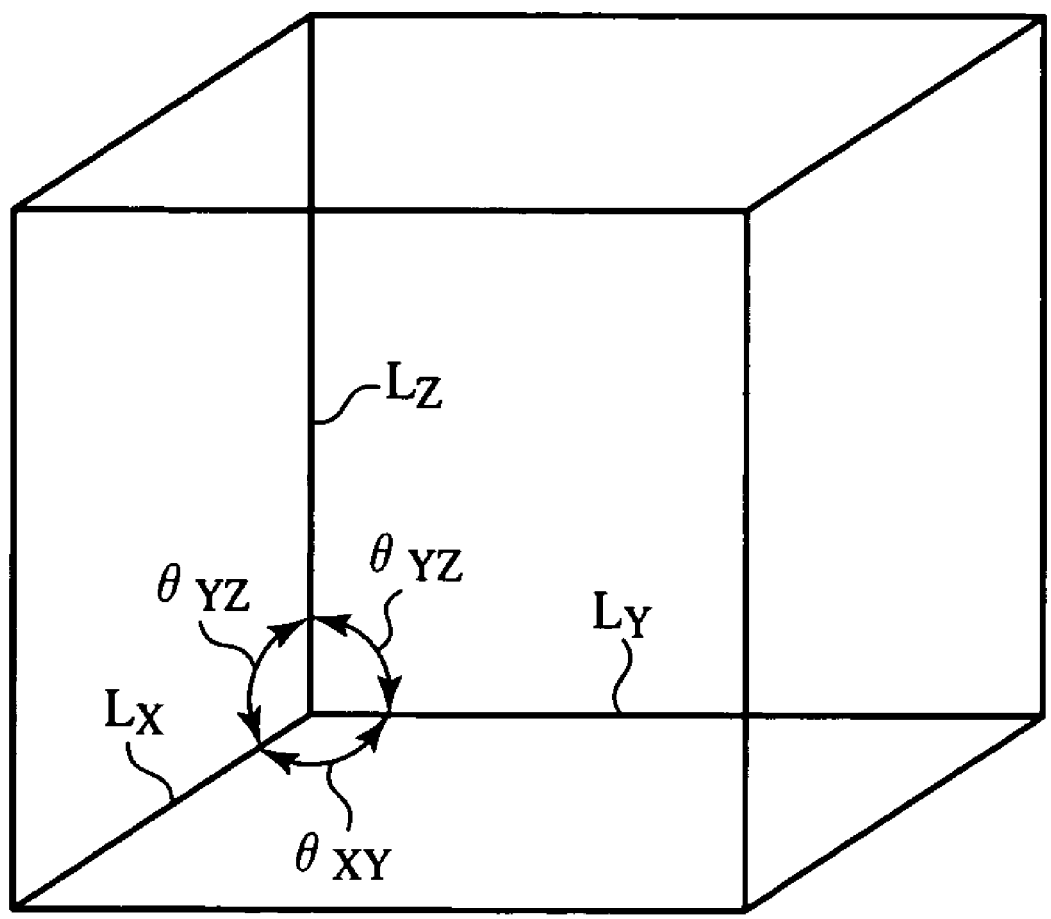
FIG. 5 is a conceptual view of a crystal structure model.

Next, the processing unit 10 displays the image of the lattice strain distribution on the screen of the display unit 18. When the lattice strain distribution is displayed, the display is made for each of the lattice strain elements. FIG. 5 is a conceptual view of a model of the crystal structure. When a model of a tree-dimensional crystal structure is considered, the lattice strain has 3 kinds of elements of the crest lengths $L_{XY}, L_{YZ}, L_{ZX}$, and 3 kinds of elements of inter-plane angles $\theta_X, \theta_Y, \theta_Z$. When a lattice strain distribution is displayed, all the 6 elements may be respectively displayed, or some of the 6 kinds of elements may be displayed in consideration of a crystal structure, and stress field symmetry.

Figure 6:
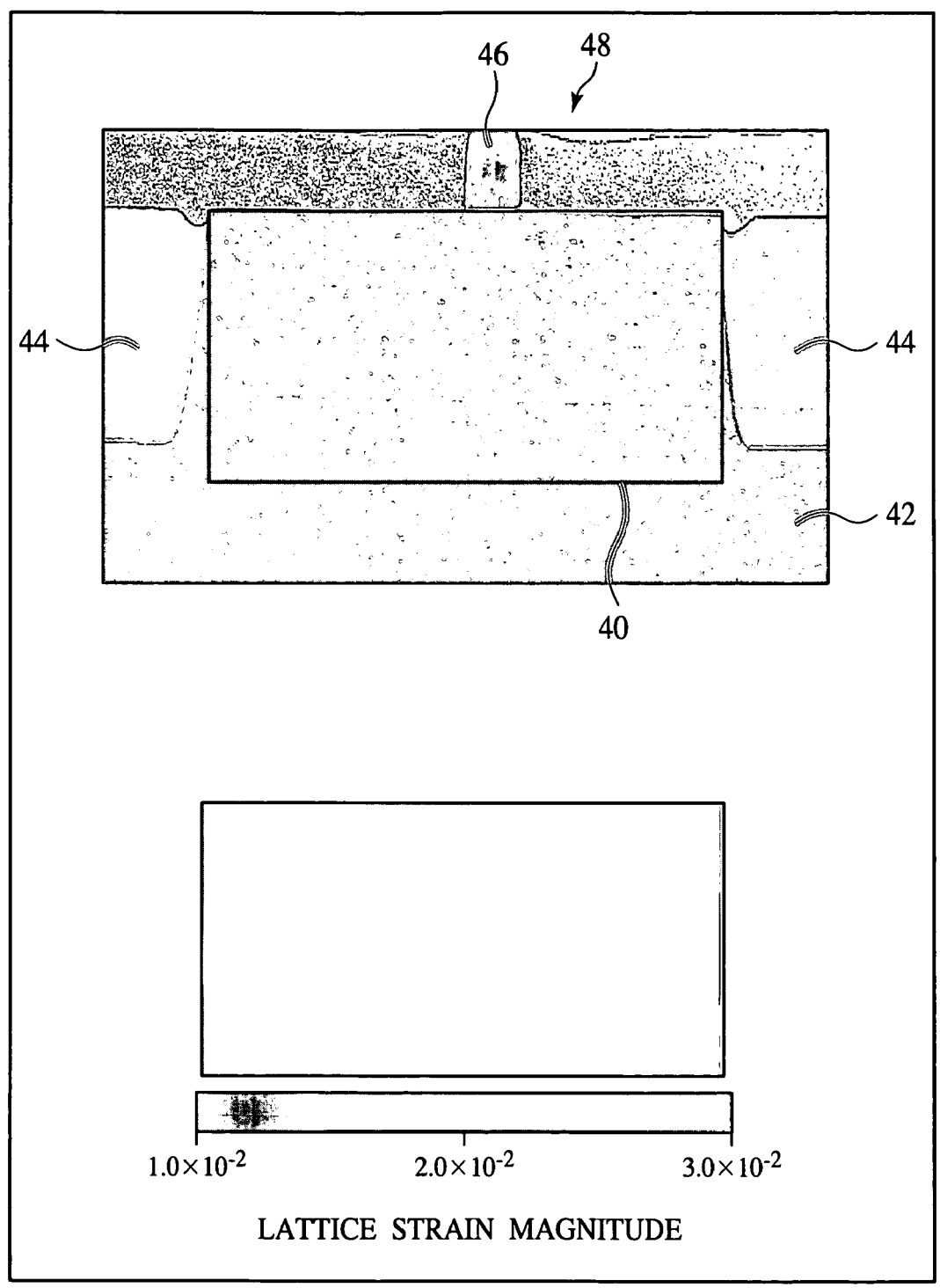
FIG. 6 is a view of one example of the display of images of an electron microscope image and a lattice strain distribution.

FIG. 6 is views of a display example of the electron microscope image and the lattice strain distribution. The upper image in FIG. 6 is the electron microscope image. The lower image in FIG. 6 is the lattice strain distribution image. The region of the upper image in FIG. 6, which is surrounded by the thick line is the region where the lattice strain measurement was made. When a lattice strain distribution image is displayed, the lattice strain distribution image is displayed associated with the electron microscope image as shown in FIG. 6. The data of an electron microscope image and the data of a lattice strain magnitude are both associated with the same coordinate system, and the lattice strain distribution image can be displayed, associated with the electron microscope image. As exemplified in FIG. 6, an electron microscope image is displayed at an upper part of the screen, and a lattice strain distribution image is displayed at a lower part of the screen. The lattice strain distribution image may be displayed, overlapping the electron microscope image.

In the present embodiment, electron beams 34 are caused to scan by, e.g., 1.5 nm to measure intensities of electron beams transmitted by a sample 32. A 1.5 nm×1.5 nm region of the sample 32 corresponds to one picture element of the electron microscope image 36. The electron microscope image shown in FIG. 6 is of a 1536 nm×960 nm region and is formed of 1024 picture elements×640 picture elements.

The region 40 of the upper image in FIG. 6, which is surrounded by the thick line, i.e., the region 40 where the lattice strain magnitude has been measured, is a 1200 nm×375 nm region. The lower image in FIG. 6, i.e., the lattice strain distribution image is formed of 800 picture elements×250 picture elements.

The size of a region of a sample 32 corresponding to one picture element, the size of a region for an electron microscope image to be taken, etc. are not limited to the above. The convergence size of the electron beams, the magnification of the electron microscope image, etc. are suitably set to thereby obtain arbitrary electron microscope images, etc.

In displaying a lattice strain distribution, the lattice strain distribution may be displayed, for example, in colors corresponding to lattice strain magnitudes. In displaying the lattice strain distribution, the lattice strain distribution may be displayed, for example, in tints of colors corresponding to lattice strain magnitudes.

Thus, the lattice strain distribution image is displayed corresponding to the electron microscope image (step S6).

The sample in the present embodiment is a semiconductor device comprising a transistor 48 including a gate electrode 46 and a source/drain diffused layer in a device region defined by a device isolation region 44 formed on a silicon substrate 42 by STI (Shallow Trench Isolation). The sample is not limited to such semiconductor device. The principle of the present invention is applicable to the measurement on any sample.

In the present embodiment, convergent-beam electron diffraction images 36 are taken at all measuring points in a region 40 for the lattice strain to be measured, and then lattice strain magnitudes at the respective measuring points were computed. However, while convergent-beam electron diffraction images 36 are being made, lattice strain magnitudes at the respective measuring points may be computed.

As described above, the lattice strain measuring system and method according to the present embodiment are characterized mainly in that convergent-beam electron diffraction images 36 are taken at respective measuring points by the scanning transmission electron microscope 12, and lattice strain magnitudes at the respective measuring points are computed based on the taken convergent-beam electron diffraction images 36, and a lattice strain distribution image is displayed, associated with an electron microscope image.

In the proposed measuring method, as described above, a sample, for example, is moved to change the incidence position of the electron beams, and it is very difficult to move the sample at a fine pitch accurately and in a short period of time. Accordingly, the proposed measuring method cannot measure lattice strain distributions of electronic devices having micronized structures of nanometer order with high resolving powers. Furthermore, in the proposed measuring method, which uses TEM (transmission electron microscopes), the convergent-beam electron diffraction images are distorted by the influence of the image forming lens disposed below a sample, which makes it impossible to measure lattice strain magnitudes with high accuracy. The proposed measuring method finds it difficult to precisely correspond measuring points to electron microscope images, and cannot be a useful guide in the device development.

According to the present embodiment, however, the STEM (scanning transmission electron microscope) 12 is used, whereby electron beams 34 are caused to thereby suitably set an incidence position of the electron beams 34. Accordingly, the incidence position of the electron beams 34 can be moved at a pitch of the nanometer order accurately and in a short period of time. The use of the scanning transmission electron microscope 12 requires no image forming lens below a sample 32, whereby the convergent-beam electron diffraction image 36 is free from the distortion due to the influence of the image forming lens. Thus, according to the present embodiment, lattice strain distributions of electronic devices of micronized structures of nanometer order can be displayed in images with high resolving power and high accuracy, and in a short period of time.

Furthermore, according to the present embodiment, the scanning transmission microscope 12 is used, whereby the data of electron microscope images 36 associated with coordinates of respective measuring points can be obtained. The data of electron microscope images and the data of lattice strain magnitudes are associated with the same coordinate system, whereby the electron microscope images and the lattice strain distribution images can be displayed, associated with each other. According to the present embodiment, lattice strain distribution images can be easily understandably displayed, associated with the electron microscope images, whereby the measurement result can be easily used as a useful guide in the device development.

A Second Embodiment

The lattice strain measuring system and method according to a second embodiment of the present invention will be explained with reference to FIGS. 1, 2, 7 and 8. The same member of the present embodiment as those of the lattice strain measuring system and method according to the first embodiment shown in FIGS. 1 to 6 are represented by the same reference numbers not to repeat or to simplify their explanation.

The lattice strain measuring system and method according to the present embodiment are characterized mainly in that relative lattice strain distributions are displayed.

(The Lattice Strain Measuring System)

First, the lattice strain measuring system according to the present embodiment will be explained with reference to FIGS. 1 and 2.

In the present embodiment, a processing unit 10 computes respective finite differences between a lattice strain magnitude at a reference point and lattice strain magnitudes at respective measuring points. A point R as the reference is set by a command inputted by an operator. The operator commands a reference point R (see FIG. 8) while watching an electron microscope image displayed on the display unit 18.

In the present embodiment, a reference point R is set by an operator, but the reference point R may be automatically set.

Thus, relative lattice strain magnitudes at respective measuring points are computed with reference to a lattice strain magnitude at a reference measuring point R. The computed relative lattice strain magnitudes are stored in a storage unit 20, associated with coordinates of the respective measuring points.

The processing unit 10 produces an image of the relative lattice strains, based on the computed relative lattice strain distribution. The data of the image of the relative lattice strain distribution produced by the processing unit is stored in the storage unit 20.

The processing unit 10 displays the relative lattice strain distribution image by the display unit 18. When the relative lattice strain distribution image is displayed, the relative lattice strain distribution image is displayed, associated with the electron microscope image.

The lattice strain measuring system according to the present embodiment is thus constituted.

(The Lattice Strain Measuring Method)

Figure 7:
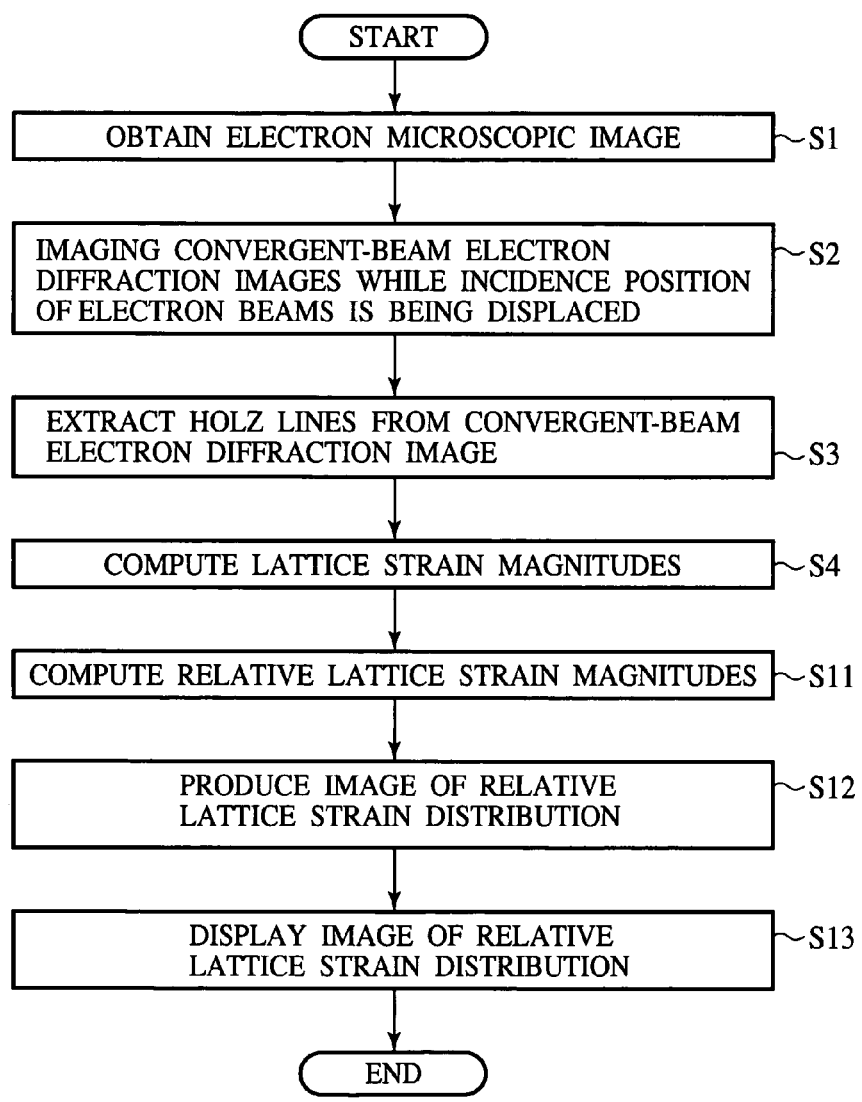
FIG. 7 is the flow chart of the lattice strain measuring method according to a second embodiment of the present invention.

Then, the lattice strain measuring method according to the present embodiment will be explained with reference to FIG. 7. FIG. 7 is the flow chart of the lattice strain measuring method according to the present embodiment.

The steps up to the step of computing absolute lattice strain magnitudes including the absolute lattice strain amount computing step are the same as the measuring method according to the first embodiment, and their explanation will not be repeated.

Then, the processing unit 10 computes finite differences between lattice strain magnitudes at respective measuring points and a lattice strain magnitude at a reference measuring point R. The reference measuring point R (see FIG. 8) is an arbitrary point. Finite differences between a lattice strain magnitude at the reference measuring point R and lattice strain magnitudes at the respective measuring points are given to thereby give relative lattice strain magnitudes (step S11).

Then, the processing unit 10 produces an image of a relative lattice strain distribution, based on the computed relative lattice strain magnitudes (step S12). The data of the produced image is stored in the storage unit 20.

Figure 8:
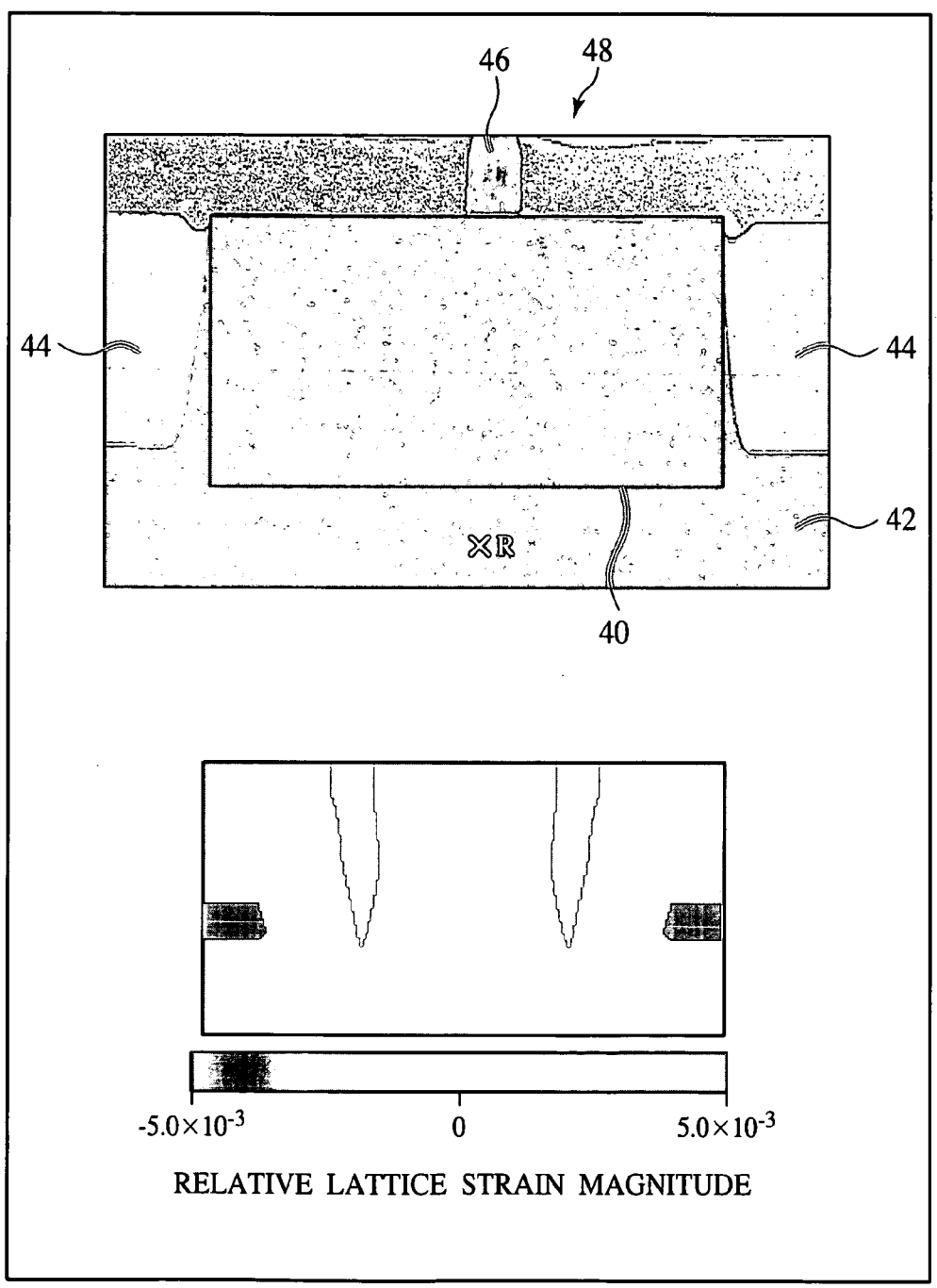
FIG. 8 is a view of one example of the display of an electron microscope image and a relative lattice strain distribution image.

Then, the processing unit 10 displays the relative lattice strain distribution image by the display unit 18 (step S13). FIG. 8 is a view of one example of a display of an electron microscope image and a relative lattice strain distribution image. A shown in FIG. 8, the relative lattice strain distribution image is displayed, associated with the electron microscope image.

The lattice strain measuring system and method according to the present embodiment is characterized mainly in that, as described above, a relative lattice strain distribution image is displayed.

According to the present embodiment, the image of a distribution of lattice strain magnitudes relative to a lattice strain magnitude at a reference measuring point R is displayed, whereby regions whose lattice strain magnitudes are larger than a lattice strain magnitude at a reference measuring point R and regions whose lattice strain magnitudes are smaller than the lattice strain magnitude at the reference measuring point R can be understandably displayed. When a point R without any lattice strain is referred to, regions having compression strains and regions having tensile strains can be understandably displayed.

A Third Embodiment

The stress measuring system and method according to a third embodiment of the present invention will be explained with reference to FIGS. 1, 2, 9 and 10. The same member of the present embodiment as those of the lattice strain measuring system and method according to the first or the second embodiment shown in FIG. 1 to 8 are represented by the same reference numbers not to repeat or to simplify their explanation.

The stress measuring system and method according to the present embodiment is characterized mainly in that stresses generated at respective measuring points are computed, based on lattice strain magnitudes given by the above-described method, and the image of a distribution of the computed stresses is displayed.

(The Stress Measuring System)

First, the stress measuring system according to the present embodiment will be explained with reference to FIGS. 1 and 2.

A processing unit 10 computes stresses generated at respective measuring points by using the following transformation formula. The following formula is a transformation formula for transforming a lattice strain amount to a stress magnitude, based on the elasticity theory.

$$\begin{Bmatrix} \sigma_{XX} \\ \sigma_{YY} \\ \sigma_{ZZ} \\ \tau_{XY} \\ \tau_{YZ} \\ \tau_{ZX} \end{Bmatrix} = \frac{(1-v)E}{(1+v)(1-2v)} \begin{bmatrix} 1 & \frac{v}{1-v} & \frac{v}{1-v} & 0 & 0 & 0 \\ \frac{v}{1-v} & 1 & \frac{v}{1-v} & 0 & 0 & 0 \\ \frac{v}{1-v} & \frac{v}{1-v} & 1 & 0 & 0 & 0 \\ 0 & 0 & 0 & \frac{1-2v}{2(1-v)} & 0 & 0 \\ 0 & 0 & 0 & 0 & \frac{1-2v}{2(1-v)} & 0 \\ 0 & 0 & 0 & 0 & 0 & \frac{1-2v}{2(1-v)} \end{bmatrix} \begin{Bmatrix} \varepsilon_{XX} \\ \varepsilon_{YY} \\ \varepsilon_{ZZ} \\ \gamma_{XY} \\ \gamma_{YZ} \\ \gamma_{ZX} \end{Bmatrix} \quad (2)$$

In the transformation formula, $\epsilon_{XX}$, $\epsilon_{YY}$, $\epsilon_{ZZ}$ respectively represent strain magnitudes in X direction, Y direction and Z direction of a crystal lattice model. $\gamma_{XY}$, $\gamma_{YZ}$, $\gamma_{ZX}$ represent strain magnitudes of angles between planes of the crystal lattice model. $\sigma_{XX}$, $\sigma_{YY}$, $\sigma_{ZZ}$ represent stresses corresponding to strain magnitudes $\epsilon_{XX}$, $\epsilon_{YY}$, $\epsilon_{ZZ}$. $\tau_{XY}$, $\tau_{YZ}$, $\tau_{ZX}$ represent stresses corresponding to strain magnitudes $\gamma_{XY}$, $\gamma_{YZ}$, $\gamma_{ZX}$. The formula for computing the stresses is not limited to Formula (2) and can be suitably set.

The processing unit 10 stores in the storage unit 20 the stress magnitudes computed by the above-described transformation formula (2), associated with coordinates of respective measuring points.

The processing unit 10 produces an image of a distribution of the stresses generated at the respective measuring points of a sample 32, based on the date of the computed stress magnitudes. The data of produced image are stored in the storage unit 10.

The processing unit 10 displays the stress distribution image by a display unit 18. When the stress distribution image is displayed, the stress distribution image is displayed, associated with the electron microscope image. The data of the electron microscope image and the data of the stress magnitudes are associated with the same coordinate system, and the stress distribution image can be displayed, associated with the electron microscope image. For example, the electron microscope image is displayed at an upper part of the display screen, and the stress distribution image is displayed at a lower part of the display screen. The stress distribution image may be displayed, overlapping the electron microscope image.

When an image of a distribution of stresses is displayed, the stresses are displayed for stress elements $\epsilon_{XX}$, $\epsilon_{YY}$, $\epsilon_{ZZ}$, $\gamma_{XY}$, $\gamma_{YZ}$, $\gamma_{ZX}$ corresponding to lattice strain elements $\sigma_{XX}$, $\sigma_{YY}$, $\sigma_{ZZ}$, $\tau_{XY}$, $\tau_{YZ}$, $\tau_{ZX}$. When a distribution of stresses is displayed, the stresses may be displayed for all the six kinds of the elements, or in consideration of a crystal structure and symmetry of stress fields, the stresses may be displayed for some of the six kinds of the elements.

Figure 10:
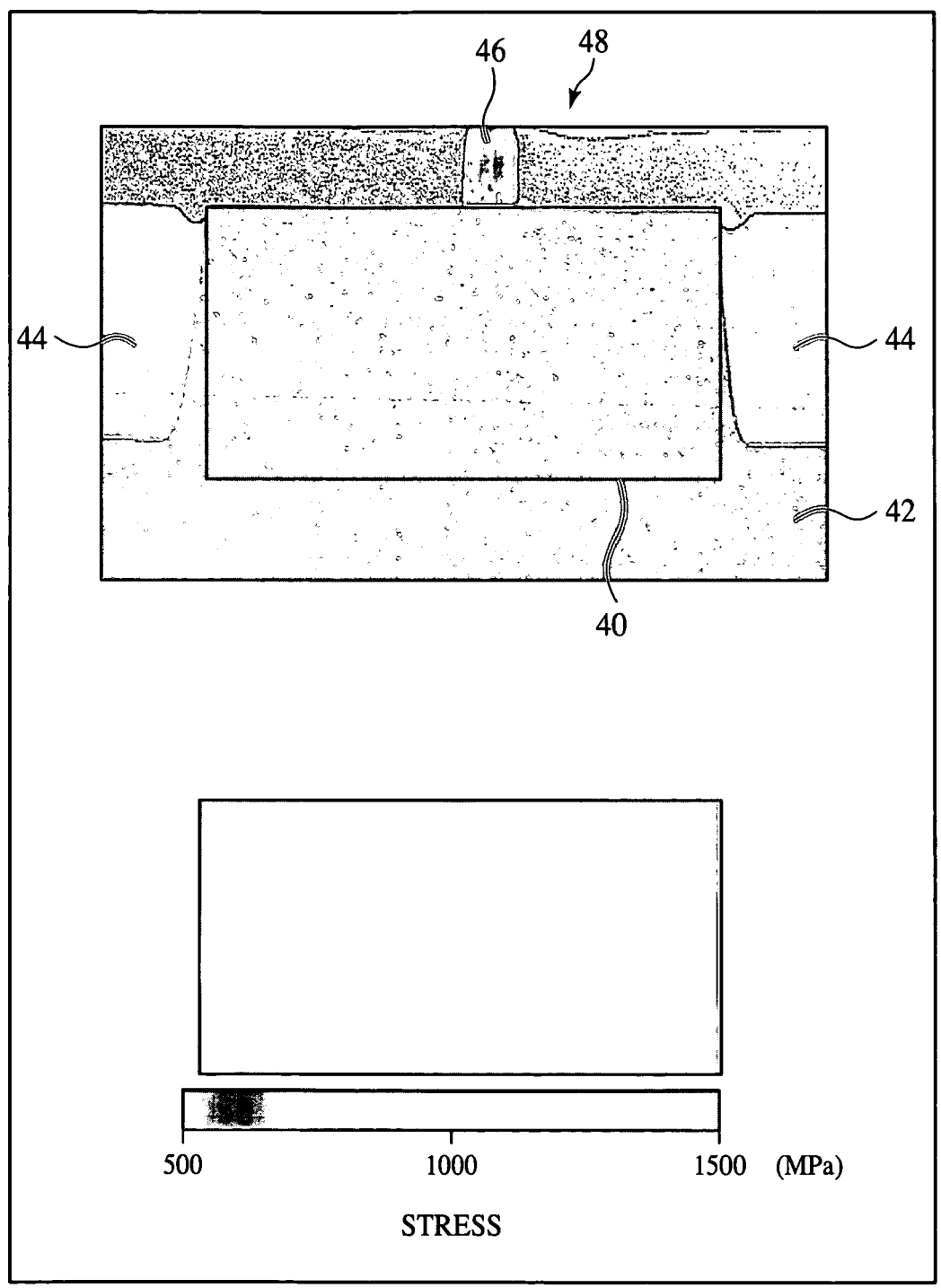
FIG. 10 is a view of one example of the display of an electron microscope image and a stress distribution image.

FIG. 10 is a view of one example of the display of an electron microscope image and a stress distribution image. The upper image in FIG. 10 is the electron microscope image, and the lower image in FIG. 10 is the stress distribution image. In the upper image in FIG. 10, the region 20 surrounded by the thick line is the region where the lattice strain measurement has been made.

When a stress distribution image is displayed, the image may be displayed in, e.g., colors corresponding to the magnitudes of the stresses. When a stress distribution image is displayed, the image may be displayed in tint of colors corresponding to the magnitudes of the stresses.

The stress measuring system according to the present embodiment is thus constituted.

(The Stress Measuring Method)

Figure 9:
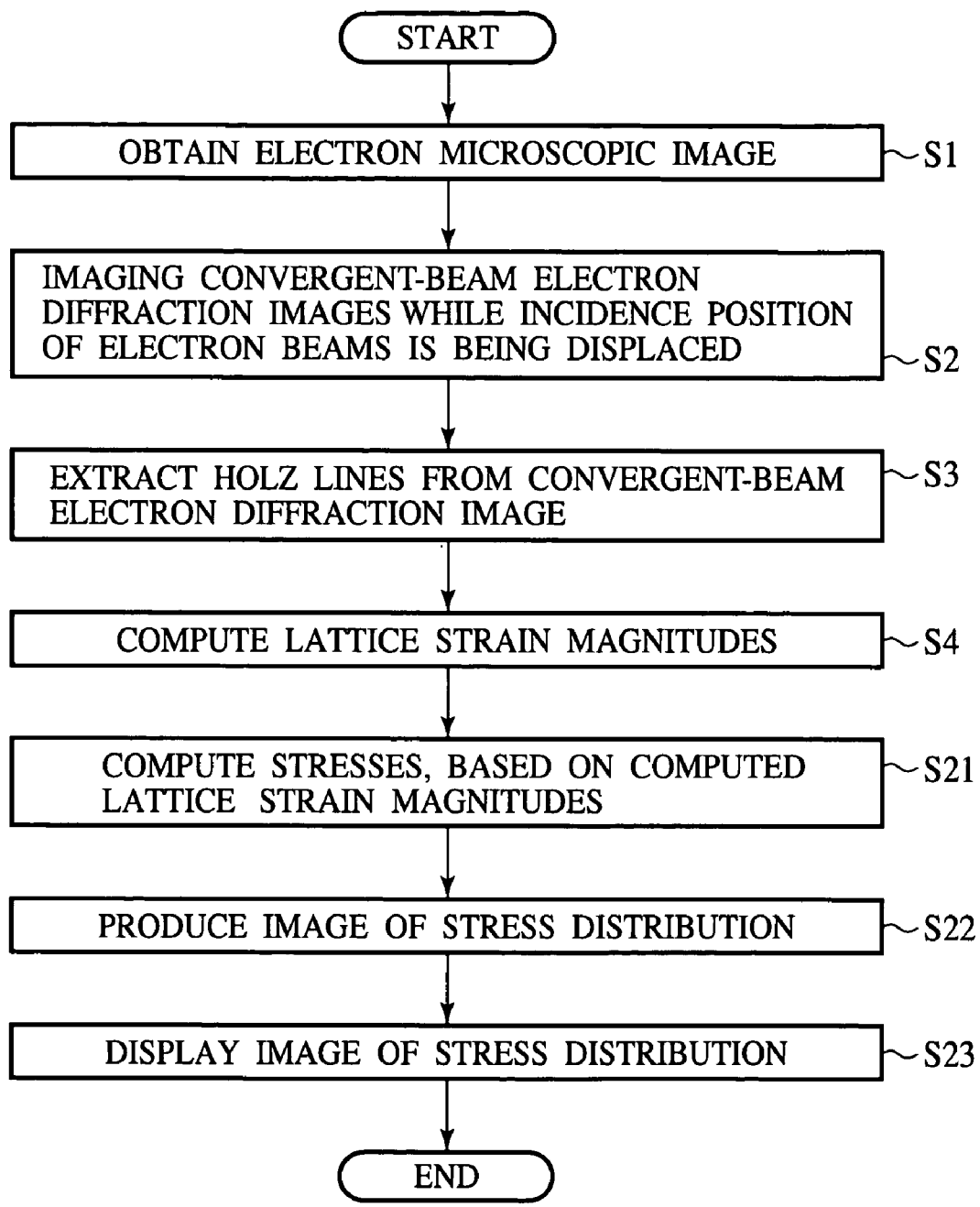
FIG. 9 is the flow chart of the stress measuring method according to a third embodiment of the present invention.

Then, the stress measuring method according to the present embodiment will be explained with reference to FIGS. 9 and 10. FIG. 9 is the flow chart of the stress measuring method according to the present embodiment.

The steps up to the step of measuring lattice strain magnitudes at respective measuring points (step S4) including the lattice strain magnitude measuring step are the same as those of the lattice strain measuring method according to the first and the second embodiments, and their explanation will not be repeated.

Then, the processing unit 10 transforms the lattice stresses at the respective measuring points to stress magnitudes by using the transformation formula (Formula 2) as described above (step S21). The data of the computed stress magnitudes are stored in the storage unit 20, associated with coordinates of the respective measuring points.

Next, the processing unit 10 produces an image of a distribution of stresses at respective measurements points, based on the computed stress magnitudes (step S22). The data of the produced image is stored in the storage unit 20.

Next, the processing unit 10 displays the stress distribution image by the display unit 18 (step S23). When the stress distribution image is displayed, the stress distribution image is displayed, associated with the electron microscope image.

As described above, according to the present embodiment, stresses generated at respective points of a sample are computed, based on lattice strain magnitudes given by the lattice strain measuring system and method according to the first embodiment, the image of a distribution of stresses generated in an electronic device of a micronized structure can be displayed with high resolving power and high accuracy and in a short period of time. Furthermore, the stress distribution image can be understandably displayed, associated with the electron microscope image, and the measurement results can be used as useful guides in device development.

A Fourth Embodiment

The stress measuring system and method according to a fourth embodiment of the present invention will be explained with reference to FIGS. 1, 2, 11 and 12. The same members of the present embodiment as those of the lattice strain measuring system and method, etc. according to the first to the third embodiments shown in FIGS. 1 to 10 are represented by the same reference numbers not to repeat or to simplify their explanation.

The stress measuring system and method according to the present embodiment is characterized mainly in that relative stress magnitudes are displayed.

(The Stress Measuring System)

First, stresses generated at respective points of a sample are computed in absolute values, as has been explained in the third embodiment.

A processing unit 10 computes infinite differences between stress magnitudes at respective measurements points and a stress magnitude at a reference point R. The reference point R is an arbitrary point. The infinite differences between the stress magnitudes at the respective measurements points and the stress magnitude at the reference point R are computed to thereby compute relative stress magnitudes.

The processing unit 10 produces an image of a distribution of the relative stress magnitudes. The data of the produced image is stored in a storage unit 20.

The processing unit 10 displays the relative stress magnitude distribution image by a display unit 18. When the relative stress magnitude distribution image is displayed, the relative stress distribution image is displayed, associated with the electron microscope image.

The stress measuring system according to the present embodiment is thus constituted.

(The Stress Measuring Method)

Figure 11:
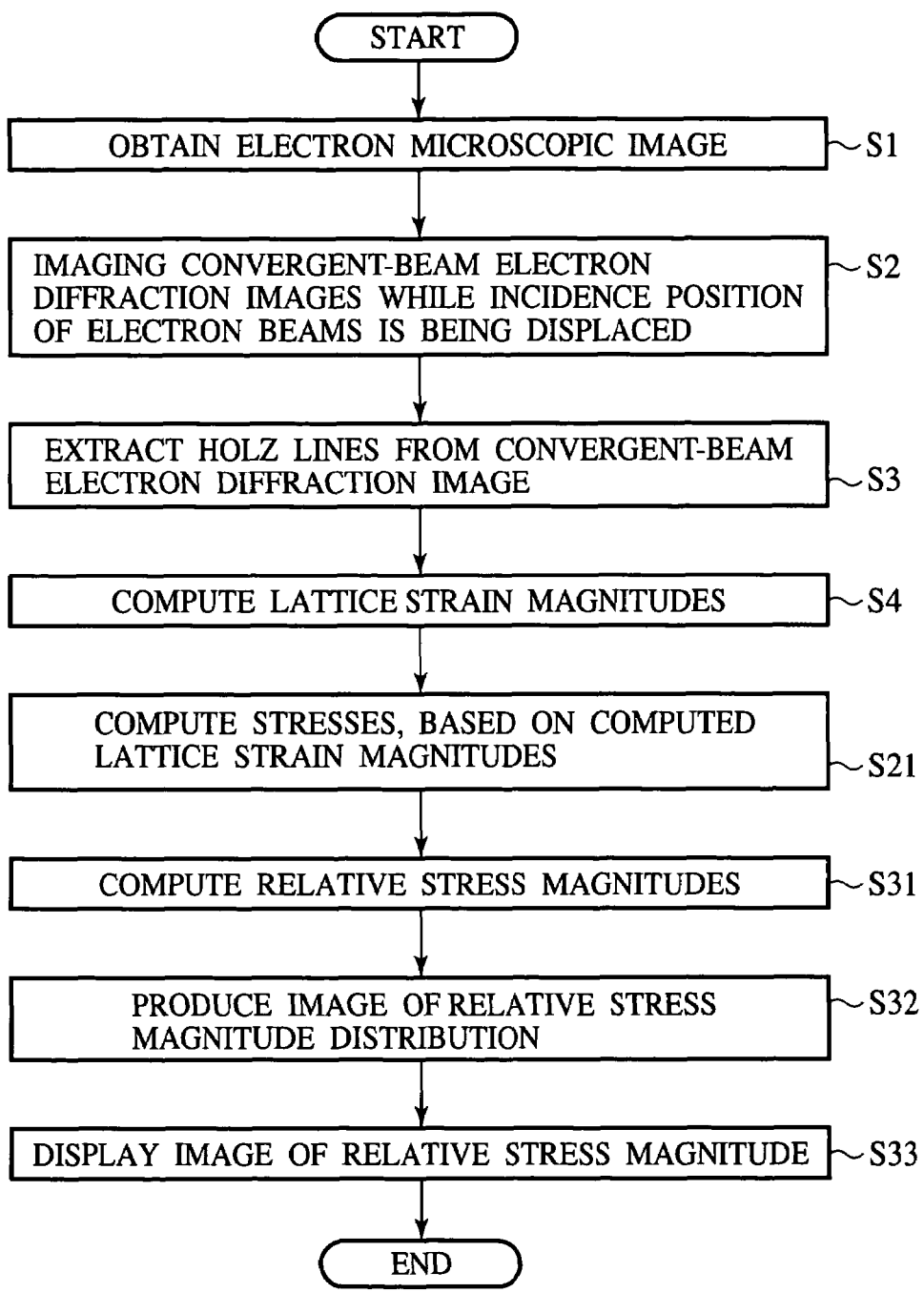
FIG. 11 is the flow chart of the stress measuring method according to a fourth embodiment of the present invention.
Figure 12:
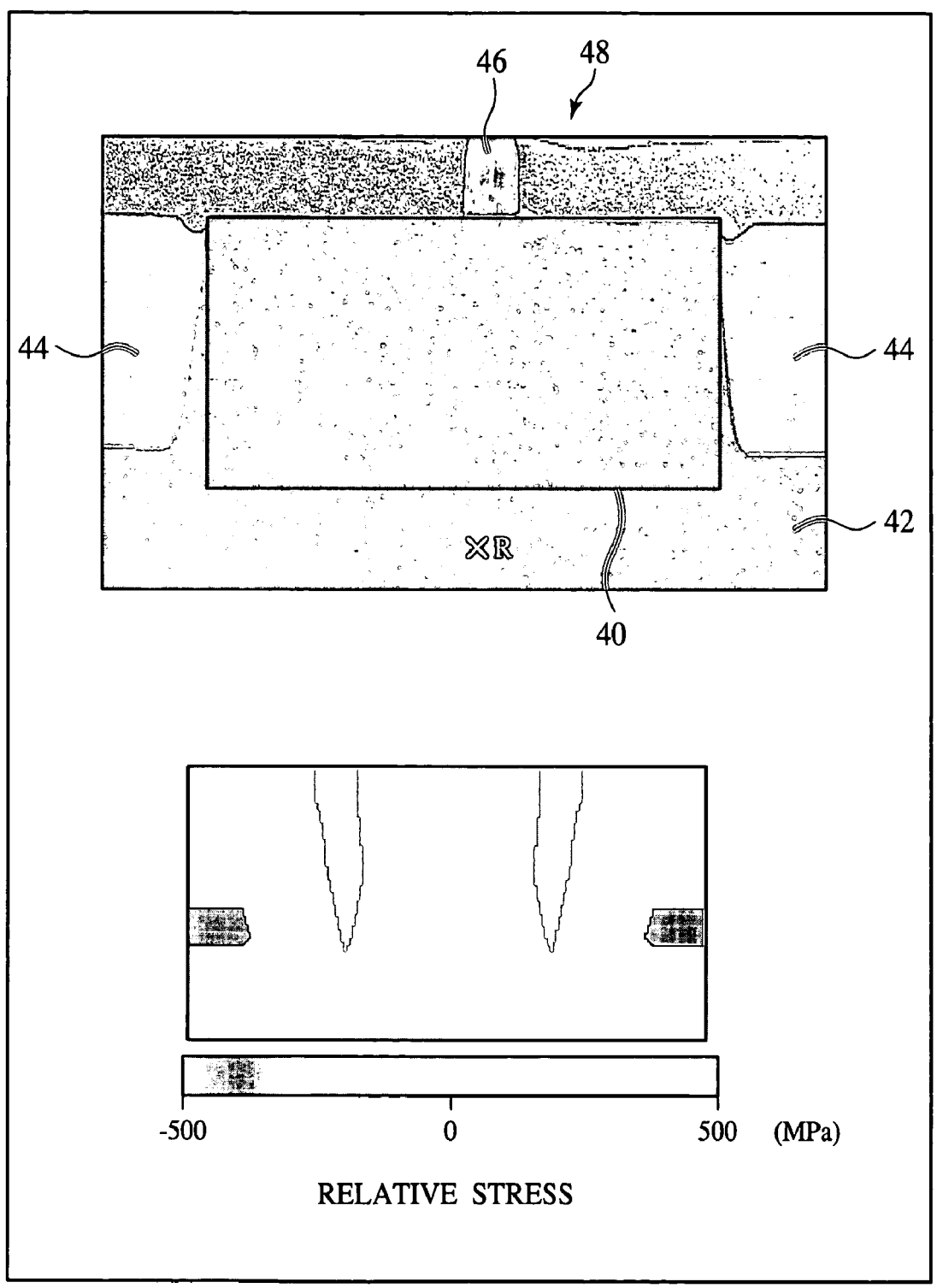
FIG. 12 is a view of one example of the display of an electron microscope image and a relative stress distribution image.

Then, the stress measuring method according to the present embodiment will be explained with reference to FIGS. 11 and 12. FIG. 11 is the flow chart of the stress measuring method according to the present embodiment. FIG. 12 is a view of one example of the display of an electron microscope image and a relative stress distribution image. The image at an upper part in FIG. 12 is the electron microscope image. The image at a lower part in FIG. 12 is of a relative stress magnitude distribution.

The steps up to the step of computing magnitudes of stresses generated at respective points by the above-described transformation formula (step S21) including the stress magnitude measuring step are the same as those of the stress measuring method according to the third embodiment, and their explanation will not be repeated.

Then, the processing unit 10 computes the infinite differences of the stress magnitudes at the respective measuring points and the stress magnitude at the reference point R. Thus, relative stresses generated at the respective measuring points of a sample 32 can be computed (step S31). The data of the computed relative stress magnitudes are stored in the storage unit 20.

Then, an image of a relative stress distribution is produced by processing unit 10, based on the computed relative stress magnitudes (step S32). The data of the produced data is stored in the storage unit 20.

Next, the processing unit 10 displays the image of the relative stress distribution by the display unit 18 (step S33) When the image of the relative stress distribution is displayed, the relative stress distribution image is displayed, associated with the electron microscope image.

Thus, the relative stress distribution image is displayed, associated with the electron microscope image.

As described above, the stress measuring system and measuring method according to the present embodiment is characterized mainly in that a distribution of relative stresses generated at respective measuring points of a sample is displayed.

According to the present embodiment, a distribution of stresses magnitudes relative to a magnitude of a stress generated at a reference point R is displayed in an image, whereby regions whose stress magnitudes are larger than the stress magnitude at the reference point R and regions whose stress magnitudes are smaller than the stress magnitude at the reference point R can be understandably displayed.

Modified Embodiments

The present invention is not limited to the above-described embodiments and can cover other various modifications.

For example, in the first and the second embodiments, a lattice strain distribution is displayed, associated with the electron microscope image but may be displayed, not associated with the electron microscope image. For example, a lattice strain distribution image alone may be displayed.

In the third and the fourth embodiments, a stress distribution image is displayed, associated with the electron microscope image but may be displayed, not associated with the electron microscope image. For example, a stress magnitude distribution image alone may be displayed.

Figure 13:
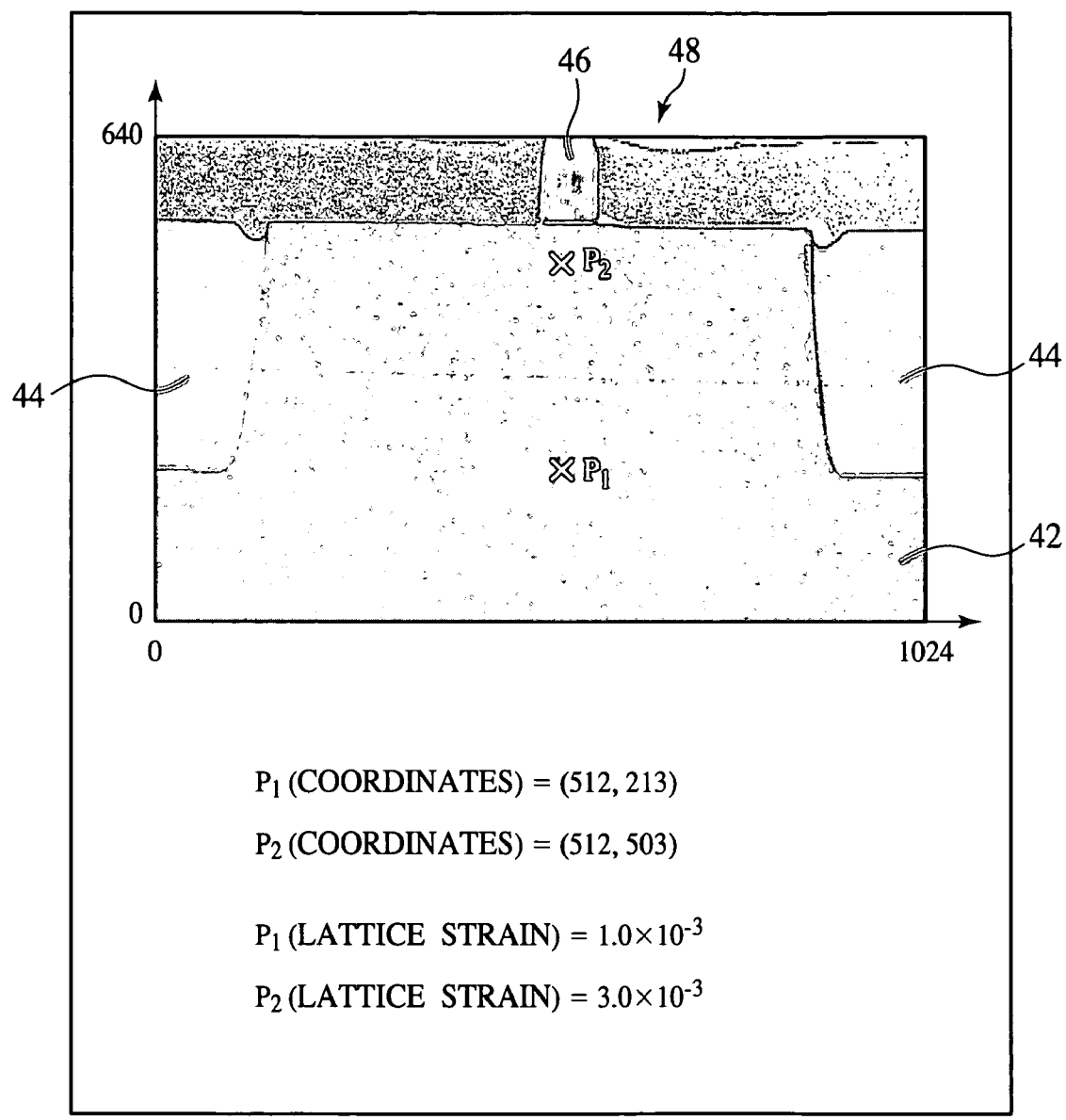
FIG. 13 is a view (part 1) of the display image of a modified embodiment of the present invention.
Figure 14:
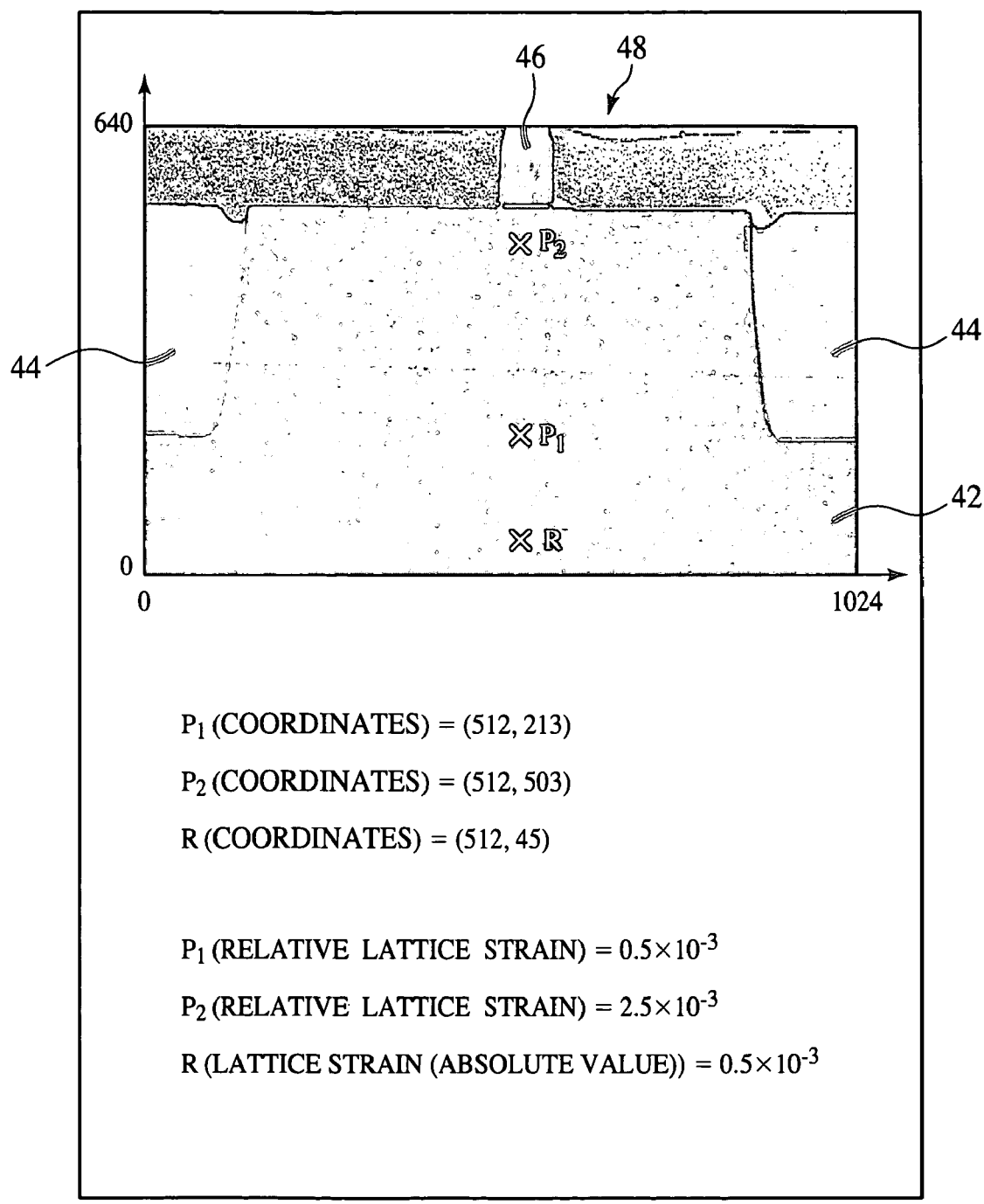
FIG. 14 is a view (part 2) of the display image of a modified embodiment of the present invention.

In the first and the second embodiments, a detailed lattice strain magnitude distribution is displayed, but a lattice strain magnitude distribution is not essentially displayed. For example, it is possible that a lattice strain magnitude at one point or lattice strain magnitudes at several points are measured, and the measured lattice strain magnitudes are displayed, associated with the electron microscope image. FIG. 13 is a view (Part 1) of a display of a modified embodiment of the present invention. As shown in FIG. 13, the lattice strain magnitude was computed at two points $P_1$, $P_2$, and the computed lattice strain magnitudes are displayed, accurately associated with the electron microscope image. It is also possible that the relative lattice strain magnitude is measured at one point or several points, and the computed relative lattice strain magnitudes are displayed, associated with the electron microscope image. FIG. 14 is a view (Part 2) of a display of a modified embodiment of the present invention. As shown in FIG. 14, the relative lattice strain magnitude is computed at two points, $P_1$, $P_2$, and the computed relative lattice strain magnitudes are displayed, accurately associated with the electron microscope image.

In the third and the fourth embodiments, magnitudes of stresses at a number of points are computed, and a distribution of the magnitudes displayed in an image. However, the stress may not be essentially computed at a number of points. For example, the stress magnitude is computed at one point or several points, and the computed magnitudes of the stresses may be displayed, associated with the electron microscope image. The relative stress magnitude is computed at one point or several points, and the computed magnitudes of the stresses may be displayed, associated with the electron microscope image.

What is claimed is:

1. A lattice strain measuring method comprising the steps of:

using a scanning transmission electron microscope to apply convergent electron beams to a sample and obtain a convergent-beam electron diffraction image of the sample, a convergent angle of the convergent electron beams being set so that high-order Laue zone lines appear in the convergent-beam electron diffraction image;

computing a lattice strain magnitude of the sample, based on the obtained convergent-beam electron diffraction image; and displaying the computed lattice strain magnitude, associated with an electron microscope image of the sample.

2. A lattice strain measuring method comprising the steps of:

using a scanning transmission electron microscope to obtain convergent-beam electron diffraction images at respective points of a sample while an incidence position of the convergent electron beams is being moved;

computing lattice strain magnitudes at the respective points of the sample, based on the obtained convergent-beam electron diffraction images; and displaying an image of a distribution of the lattice strain magnitudes of the sample, based on the computed lattice strain magnitudes.

3. A lattice strain measuring method according to claim 2, wherein in the step of displaying an image of a distribution of the lattice strain magnitudes, the image of a distribution of the lattice strain magnitudes is displayed, associated with an electron microscope image of the sample.

4. A lattice strain measuring method according to claim 2, wherein in the step of computing lattice strain magnitudes, relative lattice strain magnitudes with respect to a reference lattice strain magnitude is computed, and in the step of displaying an image of a distribution of the lattice strain magnitudes, a distribution of the relative lattice strain magnitudes is displayed.

5. A lattice strain measuring method according to claim 3, wherein in the step of computing lattice strain magnitudes, relative lattice strain magnitudes with respect to a reference lattice strain magnitude is computed, and in the step of displaying an image of a distribution of the lattice strain magnitudes, a distribution of the relative lattice strain magnitudes is displayed.

6. A stress measuring method comprising the steps of:

using a scanning transmission electron microscope to apply convergent electron beams to a sample and obtain a convergent-beam electron diffraction image of the sample;

computing a lattice strain magnitude of the sample, based on the obtained convergent-beam electron diffraction image;

computing a stress generated in the sample, based on the computed lattice strain magnitude; and displaying a magnitude of the computed stress, associated with an electron microscope image of the sample.

7. A stress measuring method comprising the steps of:

using a scanning transmission electron microscope to sequentially obtain convergent-beam electron diffraction images at respective points of a sample while an incidence position of the convergent electron beams is being moved;

computing lattice strain magnitudes of the respective points of the sample, based on the obtained convergent-beam electron diffraction images;

computing stresses generated at the respective points of the sample, based on the computed lattice strain magnitudes; and displaying an image of a distribution of the stresses generated in the sample, based on the computed stresses.

8. A stress measuring method according to claim 7, wherein in the step of displaying an image of a distribution of the stresses, the image of a distribution of the stresses is displayed, associated with an electron microscope image of the sample.

9. A stress measuring method according to claim 8, wherein in the step of computing stresses, relative stress magnitudes with respect to a reference stress magnitude are computed, and in the step of displaying an image of the distribution of the stresses, an image of a distribution of the relative stresses with respect to the prescribed reference value is displayed.

10. A stress measuring method according to claim 7, wherein in the step of computing stresses, relative stress magnitudes with respect to a reference stress magnitude are computed, and in the step of displaying an image of the distribution of the stresses, an image of a distribution of the relative stresses with respect to the prescribed reference value is displayed.

11. A lattice strain measuring system comprising:

a convergent-beam electron diffraction image taking unit which uses a scanning transmission electron microscope to apply convergent electron beams to a sample and obtain a convergent-beam electron diffraction image of the sample, a convergent angle of the convergent electron beams being set so that high-order Laue zone lines appear in the convergent-beam electron diffraction image;

a lattice strain magnitude computing unit which computes a lattice strain magnitude, based on the obtained convergent-beam electron diffraction image; and a display unit which displays the computed lattice strain magnitude, associated with an electron microscope image of the sample.

12. A lattice strain measuring system comprising:

a convergent-beam electron diffraction image taking unit which uses a scanning transmission electron microscope to sequentially obtain convergent-beam electron diffraction images of respective points of a sample while an incidence position of convergent electron beams is being displaced;

a lattice strain magnitude computing unit which computes lattice strain magnitudes at the respective points of the sample, based on the obtained convergent-beam electron diffraction images; and a display unit which displays an image of a distribution of the lattice strain magnitudes of the sample, based on the computed lattice strain magnitudes.

13. A lattice strain measuring system according to claim 12, wherein the display unit displays the image of a distribution of lattice strain magnitudes of the sample, associated with an electron microscope image of the sample.

14. A stress measuring system comprising:

a convergent-beam electron diffraction image taking unit which uses a scanning transmission electron microscope to apply convergent electron beams to a sample and obtain a convergent-beam electron diffraction image of the sample;

a lattice strain magnitude computing unit which computes a lattice strain magnitudes of the sample, based on the obtained convergent-beam electron diffraction image;

a stress computing unit which computes a magnitude of the stress generated in the sample, based on the computed lattice strain magnitude of the sample;

a display unit which displays the computed magnitude of the stress, associated with an electron microscope image of the sample.

15. A stress measuring system comprising:

a convergent-beam electron diffraction image taking unit which uses a scanning transmission electron microscope to sequentially form convergent-beam electron diffraction images of respective points of the sample while an incidence position of convergent electron beams is being displaced;

a lattice strain magnitude computing unit which computes lattice strain magnitudes at the respective points of the sample, based on the converged-beam electron diffraction images;

a stress computing unit which computes magnitudes of the stresses at the respective points of the sample, based on the computed lattice strain magnitudes; and a display unit which displays an image of a distribution of the stresses generated in the sample, based on the computed magnitudes of the stresses.

16. A stress measuring system according to claim 15, wherein the display unit displays the image of the distribution of the stresses generated in the sample, associated with an electron microscope image of the sample.

* * * * *